(12) United States Patent
Kato et al.

(10) Patent No.: US 8,206,689 B2
(45) Date of Patent: Jun. 26, 2012

(54) ORAL PREPARATION AND CHEWING GUM

(75) Inventors: Kazuhiko Kato, Tokyo (JP); Yoshinori Murakami, Tokyo (JP); Yoshiyuki Muroi, Tokyo (JP); Manabu Tonomura, Tokyo (JP); Mitsuyoshi Kashiwagi, Tokyo (JP)

(73) Assignee: Kao Corporation, Tokyo (JP)

( * ) Notice: Subject to any disclaimer, the term of this patent is extended or adjusted under 35 U.S.C. 154(b) by 1376 days.

(21) Appl. No.: 10/533,080

(22) PCT Filed: Oct. 31, 2003

(86) PCT No.: PCT/JP03/14035
§ 371 (c)(1),
(2), (4) Date: Apr. 28, 2005

(87) PCT Pub. No.: WO2004/039343
PCT Pub. Date: May 13, 2004

(65) Prior Publication Data
US 2006/0099153 A1    May 11, 2006

(30) Foreign Application Priority Data

Oct. 31, 2002  (JP) ................................. 2002-356013
Nov. 28, 2002  (JP) ................................. 2002-346534
Dec. 27, 2002  (JP) ................................. 2002-382568

(51) Int. Cl.
*A61K 8/00* (2006.01)
*A61K 8/21* (2006.01)

(52) U.S. Cl. .......................................... 424/49; 424/52

(58) Field of Classification Search .................. None
See application file for complete search history.

(56) References Cited

U.S. PATENT DOCUMENTS

| | | | |
|---|---|---|---|
| 4,363,794 A * | 12/1982 | Ochiai et al. | ..................... 424/52 |
| 5,560,905 A | 10/1996 | Lukacovic | |
| 6,303,104 B1 | 10/2001 | Winston et al. | |
| 2003/0124065 A1 * | 7/2003 | Majeti et al. | ..................... 424/49 |

FOREIGN PATENT DOCUMENTS

| | | | |
|---|---|---|---|
| EP | 1066823 | * | 2/2001 |
| JP | 1-104004 | | 4/1989 |
| JP | 1-203316 | | 8/1989 |
| JP | 1-305020 | | 12/1989 |
| JP | 4-253906 | | 9/1992 |
| JP | 8-505390 | | 6/1996 |
| JP | 8-319224 | | 12/1996 |
| JP | 9-143043 | | 6/1997 |
| JP | 9-202718 | | 8/1997 |
| JP | 10-511104 | | 10/1998 |
| JP | 11-116421 | | 4/1999 |
| JP | 2000-222707 | * | 2/2002 |
| JP | 2002-037721 | * | 2/2002 |
| JP | 2002-104948 | | 4/2002 |
| JP | 2000-222707 | * | 6/2002 |
| WO | WO 94/15579 | | 7/1994 |
| WO | WO 97/06774 | | 2/1997 |
| WO | 02/074274 | | 9/2002 |

OTHER PUBLICATIONS

Office Action issued Oct. 4, 2005, in Japanese Application No. 2003-371917.

* cited by examiner

*Primary Examiner* — Frederick Krass
*Assistant Examiner* — Snigdha Maewall
(74) *Attorney, Agent, or Firm* — Oblon, Spivak, McClelland, Maier & Neustadt, L.L.P.

(57) ABSTRACT

The invention provides an oral preparation or a chewing gum comprising an organic acid and/or inorganic acid and a fluoride ion supplying compound, wherein a light scattering layer is formed inside enamel of the teeth when the oral preparation or the chewing gum is applied to teeth. An internal tooth colored layer in the enamel is masked by the light scattering layer, and a white appearance is imparted to the teeth.

7 Claims, 2 Drawing Sheets

Longitudinal sections of bovine teeth

Light scattering layer

ORAL PREPARATION AND CHEWING GUM

FIELD OF THE INVENTION

The present invention relates to an oral preparation and a chewing gum containing a fluoride ion supplying compound.

BACKGROUND OF THE INVENTION

Discoloring of the teeth occurs owing to external factors such as adhesion of a colored substance to the teeth surface due to tartar, plaque, smoking, or daily drinking of coffee or tea; and internal factors such as aging which causes discoloration of the dentin appearing through the enamel having high transparency and use of a medicament such as tetracycline during the enamel formation stage, which discolors the enamel itself. In order to fundamentally whiten teeth, it is therefore necessary to take countermeasures against not only the external factors which form colored deposits on the surface but also the internal factors which form internal tooth discolorations.

A variety of physical or chemical methods have heretofore been reported as means for whitening the teeth. Reported as physical methods are, in addition to removal of the colored substance by polishing, a method of removing by using n-butyl ether or butyl butylate (Japanese Patent Laid-Open No. Hei 1-203316, . Japanese Patent Laid-Open No. Hei 1-104004) and a method of improving colored teeth by covering the teeth with ceramic veneers. As the chemical methods, known are a method of promoting remineralization by an oral preparation containing hydroxyapatite (Japanese Patent Laid-Open No. Hei 1-305020, . Japanese Patent Laid-Open No. Hei 9-202718), a method of bleaching with a peroxide (Japanese Patent Laid-Open No. Hei 4-253906), a method of using a dental whitening composition obtained by adding, to a peroxide, a self curing type calcium phosphate compound and a fluoride (Japanese Patent Laid-Open No. Hei 11-116421), a method of promoting remineralization of the enamel by an oral preparation containing a liquefied calcium phosphate compound (Japanese Patent Laid-Open No. Hei 8-319224), or the like.

Application of ceramic veneers needs buffing of the dental surface, whereby the use of the veneers requires guidance and treatment by a dentist. Such dental treatment by experts inevitably costs high amounts. In the method of bleaching with a peroxide, there needs to be a proper concentration of the peroxide for ensuring bleaching of the teeth, whereby such method requires careful treatments according to guidance by an expert.

The method of promoting remineralization by calcium phosphate series compounds such as hydroxyapatite, which has a function to restore the surface of enamel with apatite as its major function for normalization of the teeth, provides unsatisfied results in whitening effects.

Recently, Japanese Patent Laid-Open No. 2002-37721 discloses a method capable of imparting whiteness and gloss to the teeth surface with the use of an oral preparation comprising the following components: (A) 0.02 to 0.7 wt. % (in terms of fluorine atom) of a fluoride ion supplying component; (B) 0.1 to 5 mol/kg of an acid compound having a pKa (25° C.) of 2.5 to 6.0 and the salt thereof; and (C) 5 to 90 wt. % of water, and having a pH, as that of the preparation itself or a 30 wt. % aqueous solution thereof, ranging from 3 to 5.5. Such oral preparation as described in Japanese Patent Laid-Open No. 2002-37721 forms a layer of calcium fluoride on a surface of the teeth to provide whiteness and gloss thereto.

SUMMARY OF THE INVENTION

The present invention relates to an oral preparation and a chewing gum comprising an organic acid, inorganic acid, or mixtures thereof. The preparation and the chewing gum further comprise a fluoride ion supplying compound, wherein a light scattering layer is formed inside enamel of the teeth when the oral preparation or the chewing gum is applied to teeth.

DETAILED DESCRIPTION OF THE INVENTION

Figure 1:
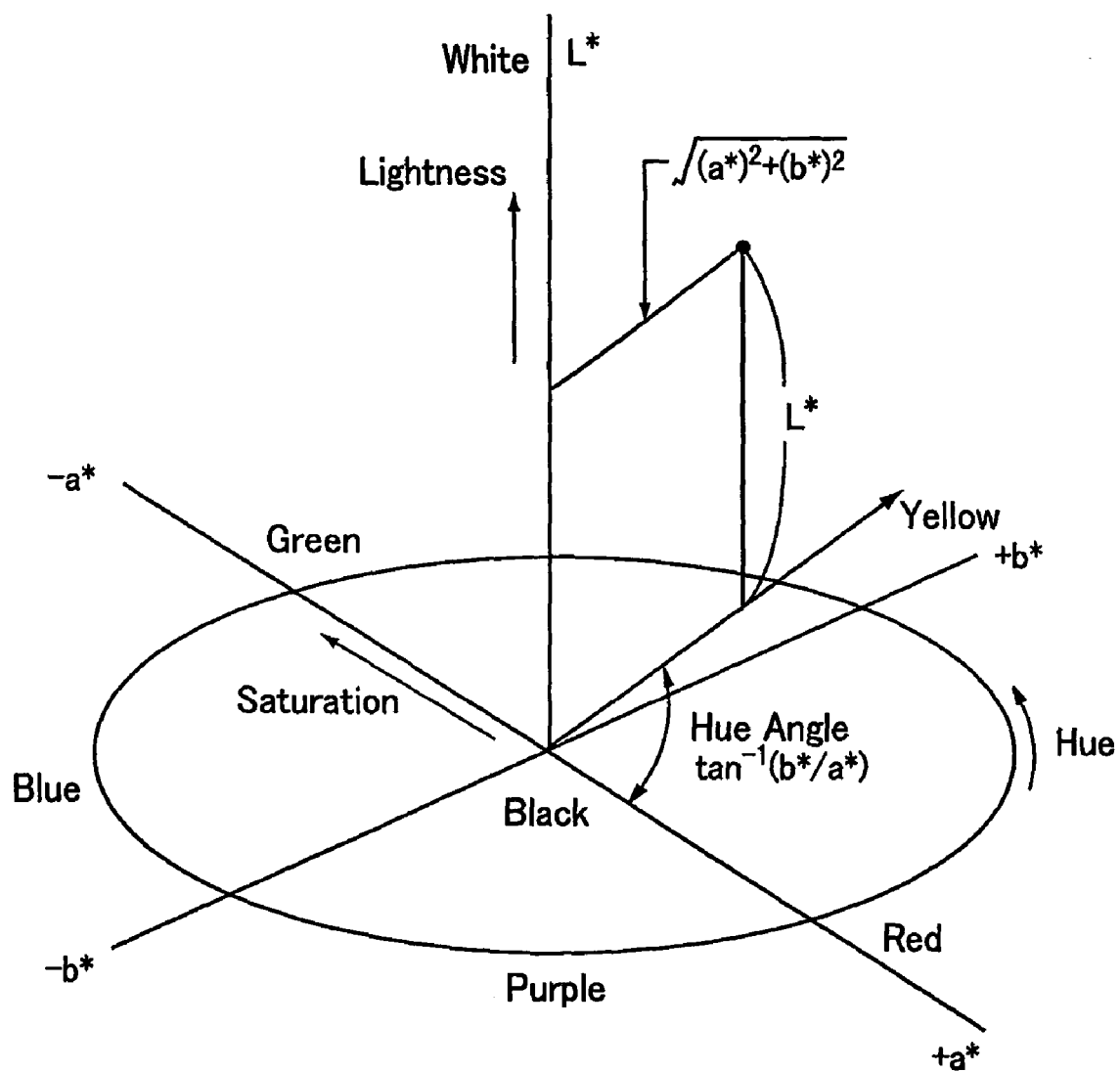
FIG. 1 shows a correlation of colors expressed by a three-dimensional coordinate system in accordance with the L*a*b* color system regulated by CIE-1976 (JIS Z8729-(1980)); and, FIG. 2 shows photographs of longitudinal sections of bovine teeth observed by a microscope. More specifically.

All publications cited herein are hereby incorporated by reference.

The present invention relates to an oral preparation and a chewing gum which are capable of forming a light scattering layer inside enamel of the teeth to mask an inner colored region of the tooth due to internal factors (hereinafter referred to as "internal tooth colored layer") when it is applied to teeth (hereinafter "oral preparation and chewing gum" may be simply referred to as "dental whitening composition".).

The present invention provides an oral preparation which gives an excellent whitening effect to the teeth by a method based on a theory quite different from conventionally known methods.

When an endogenous colored substance which is generated by internal factors is deposited in the depth of the enamel of a tooth, its color appears outward through the enamel and the tooth looks yellowish, because enamel itself is usually transparent. In this case, if a light scattering layer is formed inside the enamel of the tooth, the layer acts as a masking layer so that the tooth looks white without removal of the internal colored substances. In order to attain such advantageous effect, the masking layer is required not only to mask the endogenous colored substance which is deposited in the depth of the enamel so as not to be seen from the outside, but also to look white itself.

The present invention has realized the above idea, and provides a dental whitening composition containing at least (a) an organic acid and/or inorganic acid and (b) a fluoride ion supplying compound, wherein a light scattering layer capable of masking a deposited endogenous colored substance is formed inside enamel of the teeth when the composition is applied to the teeth. The present invention also provides a method of whitening the teeth using such dental whitening composition.

That is, when an oral preparation of the present invention is applied to the teeth, or when a chewing gum of the present invention is chewed in the mouth, calcium phosphate present in a small gap between enamel rods which make up the enamel of the teeth (hereinafter the gap is referred to as "rod gap") makes fine particles containing fluoride (hereinafter the particle is referred to as "fluoride-containing fine particles") to form a light scattering layer, which causes an irregular reflection in response to an incident light radiated from the outside. As a result, the endogenous colored substance deposited inside the enamel and having appeared there through is masked by the light scattering layer which looks white and opaque, whereby the teeth are allowed to have a white appearance.

An organic acid or inorganic acid is used to maintain a pH range acidic in an oral cavity when a dental whitening composition of the present invention is put in the mouth. No particular limitation is imposed on the organic acid or inorganic acid to be used for the dental whitening composition insofar as it is such substance as acceptable in the oral cavity.

Examples of inorganic acids include hydrochloric acid, sulfuric acid, carbonic acid, and phosphoric acid or the like. Examples of organic acids include: monobasic acid such as formic acid, acetic acid and propionic acid; dibasic acid such as oxalic acids, succinic acid, fumaric acid, adipic acid and maleic acid; hydroxycarboxylic acids such as lactic acid, glycollic acid, tartaric acid, malic acid, citric acid, ascorbic acid, gluconic acid and glyceric acid; acidic amino acids such as glutamic acid and aspartic acid; keto acids such as pyruvic acid, acetoacetic acid and levulinic acid; aromatic carboxylic acids such as benzoic acid and salicylic acid; and polycarboxylic acid such as ethylenediaminetetraacetic acid.

Two or more acids among these organic and inorganic acids may be combined when used. Moreover, to maintain the pH range in an oral cavity more stably, a buffer system may be prepared in combination of the organic acid and/or inorganic acid with the salt thereof.

Of these acids, at least one selected from the group consisting of acetic acid, lactic acid, malic acid, tartaric acid, citric acid, glycollic acid, succinic acid, and phosphoric acid, and mixtures thereof, are preferably used from the view point of bringing out effects of the present invention. In particular, lactic acid, malic acid and/or tartaric acid are more preferable in consideration of improvement of taste of the oral preparation, easiness to obtain raw materials and low cost.

In order to form a light scattering layer which has a high whitening and a high masking effect, fluoride-containing fine particles are preferably formed at a proper depth in enamel of the teeth. From this point, as the organic acid and/or inorganic acid to be incorporated in the dental whitening composition, it is preferable to use an acid which can make a buffer system keeping the pH in a range from pH 3 to pH 6 in the oral cavity where the dental whitening composition is applied. For the pH range of the above described buffer system, more preferable is a range of from pH 4 to pH 5.

As a fluoride ion supplying component, an available substance is not limited to specific ones insofar as it is acceptable in an oral cavity. Examples of fluoride ion supplying components include: inorganic fluorides such as sodium fluoride, potassium fluoride, ammonium fluoride, lithium fluoride, monofluorophosphate (e.g., sodium monofluorophosphate, potassium monofluorophosphate, ammonium monofluorophosphate, or the like); organic fluorides such as amine fluoride. Of these fluorides, sodium fluoride, sodium monofluorophosphate, stannous fluoride, lithium fluoride and ammonium fluoride are preferable in the view point of safety, solubility, taste, flavor or the like. As to the monofluorophosphate, it supplies monofluorophosphate ion first in stead of a fluoride ion, and then, the monofluorophosphate ion supplies gradually a fluoride ion.

The dental whitening composition of the present invention contains predetermined amounts of the organic acid and/or inorganic acid in order to enable a light scattering layer to be formed. However, if a large amount of these organic acids and/or inorganic acids is present in the composition such as the oral preparation or the chewing gum, an user who puts the oral preparation in his mouth or chews the chewing gum tastes a strong sour taste, so that some of the users may feel reluctant to try it because of the taste.

In contrast with this, the addition of potassium ion to the dental whitening composition of the present invention makes it possible to form a light scattering layer even if the content of the acid is small, because the potassium ion enhances the effects of the acid to be incorporated in the composition. Also, when the content of the acid to be incorporated in the dental whitening composition is reduced, the composition can improve in taste and its feeling in use.

As a component to supply the potassium ion, an available substance is not limited to specific ones insofar as it is acceptable in an oral cavity, and various kinds of potassium salts may be used. Examples of the potassium salts include potassium hydroxide, potassium fluoride, potassium chloride, potassium bromide, potassium phosphate, potassium carbonate, potassium malate, potassium citrate, potassium tartrate, potassium metaphosphate, potassium pyrophosphate, potassium sorbate, potassium nitrate, potassium aspartate, potassium alginate. From the view point of taste or storage stability, potassium hydroxide, potassium fluoride, potassium, chloride, potassium malate, potassium citrate and potassium phosphate are preferable.

The potassium ion is preferably added to the dental whitening composition as a counter ion. The addition of potassium ion may be carried out by: for example, using potassium fluoride as the fluoride ion supplying component; or preparing a buffer system by using the organic acid and/or inorganic acid in combination with potassium salt thereof or potassium hydroxide.

The content of potassium ion is preferably from 0.1 to 5 wt. %, and more preferably 0.5 to 3 wt. %, in the oral preparation to secure an excellent whitening effect of the teeth while keeping the acid concentration in the oral preparation low enough.

In addition to the above described components, the dental whitening composition of the present invention can contain, as required, one or more optional components such as foaming agent, foam booster, abrasive, humectant, binder, extender, sweetener, preservative, sterilizer, medical component, adhesive, pigment, colorant, and/or flavor. Polyethylene glycol or the like, which is a conventional whitening component, can also be used in combination.

The dental whitening composition of the present invention can take any one of forms such as solution-, gel- and paste-forms, and can be applied to an oral preparation such as tooth powder, moistened tooth powder, toothpaste, liquid dentifrice, mouthwash or the like, or a chewing gum. In any form, polyethylene glycol, propylene glycol, glycerin, sorbitol, maltitol, xylitol, lactitol or erythritol can be added as a humectant or thickener. As the thickener for the solution composition, as a gelatinizer for the gel composition, or as a binder for the paste composition, it is possible to add sodium carboxymethylcellulose, hydroxyethyl cellulose, carboxyvinyl polymer, xanthan gum, carrageenan, sodium alginate, hydroxypropyl cellulose, guar gum, sodium chondroitin sulfate, or the like. In the case where the composition has a high salt concentration owing to the buffer system, addition of a nonionic polymer such as hydroxyethyl cellulose, guar gum or hydroxypropyl cellulose may be adaptable.

As a preferred dental whitening composition that provides an especially good taste, there can be exemplified an oral preparation which is a composition containing components (A), (B), (C) and (D), and optionally containing component (E) in accordance with the following formula, and brings about a pH in a range from 3 to 5.5 when the composition is diluted to 30 wt. % with water:

(A) from 0.02 to 0.2 wt. % (in terms of fluorine atom) of the fluoride ion supplying component;
(B) from 0.03 to 0.5 mol/kg of a combination of malic acid and/or tartaric acid with salts thereof;
(C) from 0.03 to 0.5 mol/kg of potassium ion;
(D) water; and
(E) other optional components.

This formula is good in its taste, and also exhibits an improved performance to form the light scattering layer in the enamel of the teeth by means that the combined use of the malic acid and/or tartaric acid with the salts thereof, which has an excellent buffering capability, and the addition of potassium ion, which can reduce acid content, are employed, and further gives good feeling of use by suppressing the sour taste.

Though a pH condition with a range almost equal to that made by the buffer system using the malic acid and/or tartaric acid in combination with the salts thereof may be attained by the other buffer systems using the other acidic compounds, employment of the buffer system using malic acid and/or tartaric acid in combination with the salts thereof makes it possible to sufficiently form fluoride-containing fine particles even in a low acid concentration, and also possible to suppress the sour taste thus being especially advantageous in taste.

That is, the buffer system composed of the malic acid and/or tartaric acid and the salts thereof, which is the component (B), have a strong buffering capability, and show an excellent ability to maintain an oral cavity in a pH condition capable of forming the fluoride-containing fine particles. Therefore, this buffer system provides a markedly superior effect in whitening of the teeth in comparison with the other buffer system of the same concentration, and even in a case where the used amount is reduced to lower the acid concentration, the buffer system can still provide an excellent tooth whitening effect.

Moreover, both malic acid and tartaric acid are included in foods and drinks such as fruits and wines, and they are good in taste and safe as well as capable of suppressing the sour taste, whereby allowing the preparation of oral preparation with good taste.

As salts of malic acid or tartaric acid, sodium salts, potassium salts, arginine salts, or ammonium salts may be used, and alkali metal salts such as sodium salts and potassium salts are preferable. To prepare the composition of the present invention, the salt of malic acid or tartaric acid can be added directly. There may be adapted the other method, in which organic acid such as malic acid and tartaric acid and alkali compounds such as sodium hydroxide and potassium hydroxide are blended separately, then mixed together into the composition to make a buffer system which contains the acidic compounds and the salt thereof.

In the above described formula, the component (B) is preferably used as a potassium ion supplying component. In such case, a buffer system can be made by mixing malic acid and/or tartaric acid with a potassium salt thereof, or by neutralizing malic acid and/or tartaric acid with potassium hydroxide.

An amount of the malic acid and/or tartaric acid and the salt thereof in the component (B) is preferably in a range from 0.03 to 0.5 mol/kg, and more preferably from 0.05 to 0.3 mol/kg, in terms of the sum of the malic acid and/or tartaric acid and the salts thereof contained in the oral preparation of the present invention, in order to attain an excellent tooth whitening effect while sufficiently suppressing the sour taste. Furthermore, the molar ratio of acids to salts is preferably in a range from 10/1 to 1/10 to ensure a sufficient buffering capability.

The content of potassium ion, which is the component (C), is in a range preferably from 0.03 to 0.5 mol/kg, and more preferably from 0.05 to 0.3 mol/kg in the oral preparation of the present invention, in order to attain an excellent tooth whitening effect while reducing the malic acid and/or tartaric acid as the component (B) to sufficiently low concentration.

The content of water, which is the component (D), is preferably in a range from 5 to 90 wt. % in the composition of the present invention. The composition fundamentally requires to be in an aqueous solution state in order to exhibit the buffering effect.

For the oral preparation prepared according to the above described formula, it is also important that it gives the pH value in a range from pH 3 to pH 5.5 when it is diluted to 30 wt. % with water from the view point of effectively forming the fluoride-containing fine particles. The pH value of the oral preparation in the diluted condition described above is preferably set to pH 3 or more. More preferable pH is in a range from pH 4 to pH 5.

In the above described formula, the oral preparation preferably further contains an anionic surface active agent as an optional component (E) to improve the tooth whitening effect. As the anionic surface active agents, higher alkyl sulfates, N-alkyl sarcosinic acid salts and fatty acid monoglyceride monosulfates are preferable. A carbon number of an alkyl group or fatty acid residue in the surface active agents described above is preferably 8 to 24, . and more preferably 8 to 18. As salts of these surface active agents, alkali metal salts, ammonium salts and organic amine salts are preferable. The preparation of the present invention preferably contains 0.1 to 5 wt. %, and more preferably 0.2 to 2 wt. %, of the surface active agent from the view point of the tooth whitening effect.

The dental whitening composition of the present invention can be prepared in a conventional manner for a dental whitening composition in accordance with its formulation. Toothpaste may be prepared by: for example, weighing the prescribed amount of each component listed on a recipe such as purified water, abrasive, humectant, binder, flavor, preservative, sweetener, buffer components, and fluoride ion supplying component, and if necessary another medical component; mixing under predetermined conditions to swell the binder; adding the abrasive, flavor and foaming agent to the mixture, and then mixing them while degassing. The pH adjustment may be conducted after preparation as necessary.

When the dental whitening composition of the present invention or the components contained therein are brought into the teeth by applying the oral preparation to the teeth or by chewing the chewing gum, the components of the dental whitening composition are mixed with saliva in the oral cavity to make a buffer system capable of keeping a constant pH in a more stable state. Under the condition in which the buffer system made by mixing in the oral cavity is keeping the pH of the oral cavity acidic, the acid acts on the enamel of the teeth, thereby causing change of calcium phosphate present in gaps (rod gaps) between enamel rods which make up a structure of the enamel.

In this case, the components of the dental whitening composition give rise to the formation of fluoride-containing fine particles not only at the surfaces of the teeth, but also in the rod gaps.

That is, the calcium phosphate present in the rod gaps changes to the fluoride-containing fine particles to generate a partial structure having a low refractive index, and such a region as having a low refractive index forms a light scattering layer which can cause irregular reflection in response to an incident light radiated from the outside. As a result, the color of reflected light from the light scattering layer looks white, and whiteness of the teeth is accordingly improved. Moreover, the internal tooth colored layer present in the depth of the enamel of the teeth, which has been seen from the outside through the enamel originally translucent, is masked by the light scattering layer which looks white and opaque as described above, whereby the color of the colored layer becomes invisible from the outside.

Therefore, the irregular reflection action and the masking action, both of which are brought about the light scattering layer inside the enamel, associatively affect the teeth. Thus the teeth are allowed to have a white and beautiful appearance.

In general, the light scattering layer in the enamel of the teeth is formed at a depth of 500 μm or less from the surface of the enamel. To attain sufficient whiteness and a masking effect, thickness of the light scattering layer is preferably 50 μm or more.

The fluoride-containing fine particle, which is formed by reacting the fluoride ions from the fluoride ion supplying compounds with components of the teeth or saliva in an oral cavity under the condition of keeping a constant acidic pH range in an oral cavity, is mainly composed of calcium fluoride and generally contains other components such as a calcium phosphate-fluoride complex or the like.

Although not wanting to be limited by theory, when the potassium ion is incorporated in the dental whitening composition, an ionic radius of the potassium ion is larger than sodium ion or lithium ion, and a bond to the acid in the composition is weakened. Moreover, in a case of exchanging bivalent calcium ion of hydroxyapatite for univalent potassium ion, a disproportion of charge is generated. Therefore, it is generally thought that instead of phosphate ion, carbonate ion or hydrogenphosphate ion enters into as a counter ion so that the hydroxyapatite crystal is liable to be broken. This fact or presumption means that addition of potassium ion makes the acid in the dental whitening composition improve its dissolving power against the hydroxyapatite.

That is, since presence of the potassium ion makes the dissolving power of the acid against the hydroxyapatite higher, the reactivity of the potassium phosphate exiting in the rod gaps in the enamel becomes higher even when the amount of the organic acid and/or inorganic acid in the composition is decreased, thereby maintaining behavior of formation of the fluoride-containing fine particles in the rod gaps. As a result, the addition of potassium ion to the composition makes it possible to reduce the content of the organic acid and/or inorganic acid in the dental whitening composition without degradation of an ability to form the light scattering layer.

As mentioned above, when the dental whitening composition of the present invention is applied to an oral cavity, it exhibits an excellent whitening effect toward an endogenous discoloration generated inside the teeth. Therefore, whitening of the teeth can be easily performed by a routine treatment of an oral cavity or a favorite tasting chewing gum so that the dental whitening composition of the present invention is quite useful.

In particular, when the potassium ion is added to the dental whitening composition of the present invention, and more preferably, when the buffer system comprising the malic acid and/or tartaric acid in combination with the salts thereof is used as well as the addition of the potassium ion, the composition has a weak sour taste by itself, and the taste-factors other than the sour taste are also mild, and feeling of use is accordingly improved. The adjustment of taste is also possible by adding sweetener or flavor, or the like. Therefore, the present invention can provide a dental whitening composition, which gives good feeling for user superior to the feelings of use given by the conventional compositions.

EXAMPLE

The following examples further describe and demonstrate embodiments of the present invention. The examples are given solely for the purpose of illustration and are not to be construed as limitations of the present invention.

Example A Series

<Preparation of Oral Preparation>

Toothpastes of Examples A1-1 to A1-3 and Comparative Examples A1-1 to A1-3 were prepared according to compositions as shown in Table A1. Liquid dentifrices of Examples A2-1 to A2-3 and Comparative Examples A2-1 to A2-3 were prepared according to compositions as shown in Table A2. Mouthwashes of Examples A3-1 to A3-3 and Comparative Examples A3-1 to A3-3 were prepared according to compositions as shown in Table A3. Mouth refreshers of Examples A4-1 to A4-3 and Comparative Examples A4-1 to A4-3 were prepared according to compositions as shown in Table A4. Chewing gums of Examples A5-1 to A5-3 and Comparative Examples A5-1 to A5-3 were prepared according to compositions as shown in Table A5.

TABLE A1

| | Toothpaste | | | | | |
|---|---|---|---|---|---|---|
| | EXAMPLE | | | COMPARATIVE EXAMPLE | | |
| Component (wt %) | A1-1 | A1-2 | A1-3 | A1-1 | A1-2 | A1-3 |
| Malic acid | 2 | | 1 | 2 | | 10 |
| Tartaric acid | | 2 | | | | |
| Citric acid | | | 0.5 | | | |
| Sodium fluoride | 0.21 | 0.1 | 0.21 | | 0.21 | 0.21 |
| Sodium monofluorophosphate | | 0.35 | | | | |
| Sorbit solution | 30 | 30 | 30 | 30 | 30 | 30 |
| PEG600 | 5 | 5 | 5 | 5 | 5 | 5 |
| Sodium saccharin | 0.1 | 0.1 | 0.1 | 0.1 | 0.1 | 0.1 |
| Sodium carboxy methylcellulose | 1.5 | 1.5 | 1.5 | 1.5 | 1.5 | 1.5 |

TABLE A1-continued

Toothpaste

| Component (wt %) | EXAMPLE | | | COMPARATIVE EXAMPLE | | |
|---|---|---|---|---|---|---|
| | A1-1 | A1-2 | A1-3 | A1-1 | A1-2 | A1-3 |
| Thickening silica | 5 | 5 | 5 | 5 | 5 | 5 |
| Abrasive silica | 15 | 15 | 15 | 15 | 15 | 15 |
| Sodium laurylsulfate | 1.5 | 1.5 | 1.5 | 1.5 | 1.5 | 1.5 |
| Flavor | 1 | 1 | 1 | 1 | 1 | 1 |
| pH regulator (KOH solution) | q.s.*1 | q.s.*1 | q.s.*1 | q.s.*1 | q.s.*1 | q.s.*1 |
| Purified water | q.s.*1 | q.s.*1 | q.s.*1 | q.s.*1 | q.s.*1 | q.s.*1 |
| (Total) | 100 | 100 | 100 | 100 | 100 | 100 |
| pH | 5.0 | 5.0 | 4.0 | 5.0 | 7.0 | 5.0 |
| light scattering layer | ○ | ○ | ○ | X | X | X |
| whitening effect | ⊚ | ⊚ | ⊚ | X | X | ○ |

*1 quantum sufficit

TABLE A2

Liquid dentifrice

| Component (wt %) | EXAMPLE | | | COMPARATIVE EXAMPLE | | |
|---|---|---|---|---|---|---|
| | A2-1 | A2-2 | A2-3 | A2-1 | A2-2 | A2-3 |
| Malic acid | 2 | | 1 | 2 | | 10 |
| Tartaric acid | | 2 | | | | |
| Citric acid | | | 0.5 | | | |
| Sodium fluoride | 0.21 | 0.1 | 0.21 | | 0.21 | 0.21 |
| Sodium monofluorophosphate | | 0.35 | | | | |
| Sorbit solution | 30 | 30 | 30 | 30 | 30 | 30 |
| PEG600 | 5 | 5 | 5 | 5 | 5 | 5 |
| Sodium saccharin | 0.1 | 0.1 | 0.1 | 0.1 | 0.1 | 0.1 |
| Sodium carboxy methylcellulose | 0.6 | 0.6 | 0.6 | 0.6 | 0.6 | 0.6 |
| Thickening silica | 2 | 2 | 2 | 2 | 2 | 2 |
| Abrasive silica | 15 | 15 | 15 | 15 | 15 | 15 |
| Sodium laurylsulfate | 1.5 | 1.5 | 1.5 | 1.5 | 1.5 | 1.5 |
| Flavor | 1 | 1 | 1 | 1 | 1 | 1 |
| pH regulator (KOH solution) | q.s.*1 | q.s.*1 | q.s.*1 | q.s.*1 | q.s.*1 | q.s.*1 |
| Purified water | q.s.*1 | q.s.*1 | q.s.*1 | q.s.*1 | q.s.*1 | q.s.*1 |
| (Total) | 100 | 100 | 100 | 100 | 100 | 100 |
| pH | 5.0 | 5.0 | 4.5 | 5.0 | 6.0 | 5.0 |
| light scattering layer | ○ | ○ | ○ | X | X | X |
| whitening effect | ⊚ | ⊚ | ⊚ | X | X | ○ |

*1 quantum sufficit

TABLE A3

Mouthwash

| Component (wt %) | EXAMPLE | | | COMPARATIVE EXAMPLE | | |
|---|---|---|---|---|---|---|
| | A3-1 | A3-2 | A3-3 | A3-1 | A3-2 | A3-3 |
| Malic acid | 2 | | 1 | 2 | | 10 |
| Tartaric acid | | 2 | | | | |
| Citric acid | | | 0.5 | | | |
| Sodium fluoride | 0.21 | 0.1 | 0.21 | | 0.21 | 0.21 |
| Sodium monofluorophosphate | | 0.35 | | | | |
| Sorbit solution | 30 | 30 | 30 | 30 | 30 | 30 |
| Sodium saccharin | 0.01 | 0.01 | 0.01 | 0.01 | 0.01 | 0.01 |
| Ethanol | 5 | 5 | 5 | 5 | 5 | 5 |
| Polyoxyethylene hydrogenated castor oil | 0.5 | 0.5 | 0.5 | 0.5 | 0.5 | 0.5 |
| Flavor | 0.2 | 0.2 | 0.2 | 0.2 | 0.2 | 0.2 |

TABLE A3-continued

Mouthwash

| Component (wt %) | EXAMPLE | | | COMPARATIVE EXAMPLE | | |
|---|---|---|---|---|---|---|
| | A3-1 | A3-2 | A3-3 | A3-1 | A3-2 | A3-3 |
| pH regulator (KOH solution) | q.s.*1 | q.s.*1 | q.s.*1 | q.s.*1 | q.s.*1 | q.s.*1 |
| Purified water | q.s.*1 | q.s.*1 | q.s.*1 | q.s.*1 | q.s.*1 | q.s.*1 |
| (Total) | 100 | 100 | 100 | 100 | 100 | 100 |
| pH | 4.5 | 5.0 | 4.5 | 5.0 | 6.0 | 5.0 |
| light scattering layer | ○ | ○ | ○ | X | X | X |
| whitening effect | ◎ | ◎ | ◎ | X | X | ○ |

*1 quantum sufficit

TABLE A4

Mouthrinse

| Component (wt %) | EXAMPLE | | | COMPARATIVE EXAMPLE | | |
|---|---|---|---|---|---|---|
| | A4-1 | A4-2 | A4-3 | A4-1 | A4-2 | A4-3 |
| Malic acid | 2 | | 1 | 2 | | 10 |
| Tartaric acid | | 2 | | | | |
| Citric acid | | | 0.5 | | | |
| Sodium fluoride | 0.21 | 0.1 | 0.21 | | 0.21 | 0.21 |
| Sodium monofluorophosphate | | 0.35 | | | | |
| Sorbit solution | 15 | 15 | 15 | 15 | 15 | 15 |
| Sodium saccharin | 0.02 | 0.02 | 0.02 | 0.02 | 0.02 | 0.02 |
| Ethanol | 30 | 30 | 30 | 30 | 30 | 30 |
| Sucrose fatty acid ester | 1 | 1 | 1 | 1 | 1 | 1 |
| Flavor | 1 | 1 | 1 | 1 | 1 | 1 |
| pH regulator (KOH solution) | q.s.*1 | q.s.*1 | q.s.*1 | q.s.*1 | q.s.*1 | q.s.*1 |
| Purified water | q.s.*1 | q.s.*1 | q.s.*1 | q.s.*1 | q.s.*1 | q.s.*1 |
| (Total) | 100 | 100 | 100 | 100 | 100 | 100 |
| pH | 4.5 | 5.0 | 4.5 | 5.0 | 6.0 | 5.0 |
| light scattering layer | ○ | ○ | ○ | X | X | X |
| whitening effect | ◎ | ◎ | ◎ | X | X | ○ |

*1 quantum sufficit

TABLE A5

Chewing gum

| Component (wt %) | EXAMPLE | | | COMPARATIVE EXAMPLE | | |
|---|---|---|---|---|---|---|
| | A5-1 | A5-2 | A5-3 | A5-1 | A5-2 | A5-3 |
| Malic acid | 2 | | 1 | 2 | | 10 |
| Tartaric acid | | 2 | | | | |
| Citric acid | | | 0.5 | | | |
| Sodium fluoride | 0.21 | 0.1 | 0.21 | | 0.21 | 0.21 |
| Sodium monofluorophosphate | | 0.35 | | | | |
| Gum base | 20 | 20 | 20 | 20 | 20 | 20 |
| Maltitol | 50 | 50 | 50 | 50 | 50 | 50 |
| Xylitol | 20 | 20 | 20 | 20 | 20 | 20 |
| Flavor | 2 | 2 | 2 | 2 | 2 | 2 |
| pH regulator (KOH solution) | q.s.*1 | q.s.*1 | q.s.*1 | q.s.*1 | q.s.*1 | q.s.*1 |
| Purified water | q.s.*1 | q.s.*1 | q.s.*1 | q.s.*1 | q.s.*1 | q.s.*1 |
| (Total) | 100 | 100 | 100 | 100 | 100 | 100 |
| pH | 5.0 | 4.0 | 3.5 | 5.0 | 6.0 | 5.0 |
| light scattering layer | ○ | ○ | ○ | X | X | X |
| whitening effect | ◎ | ◎ | ◎ | X | X | ○ |

*1 quantum sufficit

<Evaluating Method>

(1) Presence or No-Presence of Light Scattering Layer

The each composition as shown in Table A1 and Table A2 was diluted with ion-exchanged water to 30 wt. %, then a bovine tooth (having a mirror polished surface) was immersed in the diluted solution for 40 hours. Also, another bovine tooth (having a mirror polished surface) was immersed in the each composition shown in Table A3 and Table A4 for 40 hours. For Table A5, . the each chewing gum was cut into small pieces, next, ion-exchanged water was added to the cut pieces of the gum to adjust 30 wt. %, then stirred for long enough time. Then another bovine tooth (having a mirror polished surface) was immersed in the resultant solution for 40 hours.

Changes of the whiteness of the immersed bovine tooth was measured by a color-difference meter, the color difference was expressed on the bases of a $L^*a^*b^*$ color system regulated by CIE-197 6 (JIS Z8729-(1980)). By three-dimensional coordinate using the $L^*a^*b^*$, correlation of colors can be shown as a scale close to color sensation (FIG. 1). In FIG. 1, vertical axis $L^*$ represents lightness (or "value" in other terms), and $a^*$, $b^*$ represent chromaticity. In $L^*a^*b^*$ color system, closer to 0 (zero) the value of $b^*$ is, more weaken the yellowish color becomes, and it means white color becomes increased in intensity.

As shown in Table A6, . by the treatment of the oral preparation of the present invention, $b^*$ was decreased widely, and closed to almost 0 (zero). This fact means the tooth piece lost yellowness and attained whiteness.

TABLE A6

|  | $L^*$ | $a^*$ | $b^*$ |
| --- | --- | --- | --- |
| Treatment with the present invention | 76.07 | 5.05 | 2.82 |
| No treatment | 77.53 | 5.88 | 9.56 |
| Color difference | −1.51 | −0.51 | −5.96 |

Figures 2A, 2B, 2C:
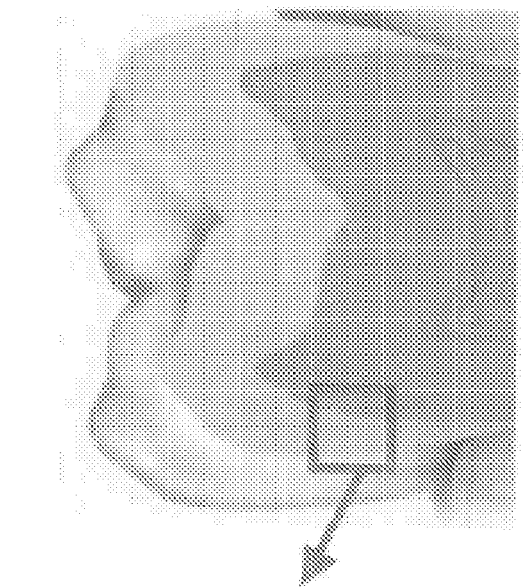
FIG. 2(a) shows a longitudinal section of a bovine tooth which was treated by an oral preparation of the present invention.
FIG. 2(b) shows a longitudinal section of a bovine tooth which was not treated by the oral preparation.
FIG. 2(c) shows a longitudinal section of bovine teeth observed by a microscope and photographed for FIG. 2(a) and FIG. 2(b).

Each tooth, which was treated by the oral preparation of the each Example, was measured by color-difference meter and confirmed that it was turned white (Table A6). The bovine tooth that was confirmed to become white was cut, then a photograph of the longitudinal section was taken by microscope. By observation on the photograph, whether a light scattering layer was formed or not under the surface of enamel was confirmed (FIG. 2). A sample which had a light scattering layer (like as FIG. 2(a)) was shown as "◯", a sample which did not have any light scattering layer (like as FIG. 2(b)) was shown as "×".

(2) Presence or No-Presence of Whitening Effect

The each composition as shown in Table A1 and Table A2 was diluted with ion-exchanged water to 30 wt. %, then a bovine tooth (having a mirror polished surface), which had been photographed in advance, was immersed in the diluted for 40 hours. Also, another bovine tooth (having a mirror polished surface), which had been photographed in advance, was immersed in the each position shown in Table A3 and Table A4 for 40 hours. For Table A5, . the each chewing gum was cut into small pieces, next ion-exchanged water was added to the cut pieces of the gum to adjust 30 wt. %, then stirred for long enough time. Another bovine tooth (having a mirror polished surface), which had been photographed in advance, was immersed in the resultant solution for 40 hours.

After the treatment, the tooth was taken out from the solution and photographed again. A panel of 15 experts was asked to see the photographs of the tooth before and after the treatment. The tooth which all of them judged to turn white was evaluated as "◎", the tooth which more than half of them judged to turn white was evaluated as "◯", remaining teeth were evaluated as "×". The each result is shown in Tables A1-A5.

<Overall Results>

The toothpastes of Examples A1-1 to A1-3 exhibited a formation of the light scattering layer inside the enamel of the teeth and whitening effect. In contrast, because the toothpaste of Comparative Example A1-1 contained the organic acid but the fluoride ion supplying compound, and that of Comparative Example A1-2 contained the fluoride ion supplying compound but the organic acid nor inorganic acid, and that of Comparative Example A1-3 contained an excessively large amount of the organic acid, these Comparative Examples A1-1 to A1-3 did not exhibit a formation of the light scattering layer inside the enamel of the teeth.

The liquid dentifrices of Examples A2-1 to A2-3 exhibited a formation of the light scattering layer inside the enamel of the teeth and whitening effect. By contrast, because the liquid dentifrice of Comparative Example A2-1 contained the organic acid but the fluoride ion supplying compound, and that of Comparative Example A2-2 contained the fluoride ion supplying compound but the organic acid nor inorganic acid, and that of Comparative Example A2-3 contained an excessively large amount of the organic acid, these Comparative Example A2-1 to A2-3 did not exhibit a formation of the light scattering layer inside the enamel of the teeth.

The mouthwashes of Examples A3-l to A3-3 exhibited a formation of the light scattering layer inside the enamel of the teeth and whitening effect. In contrast, because the mouthwash of Comparative Example A3-1 contained the organic acid but the fluoride ion supplying compound, and that of Comparative Example A3-2 contained the fluoride ion supplying compound but the organic acid nor inorganic acid, and that of Comparative Example A3-3 contained an excessively large amount of the organic acid, these Comparative Examples A3-1 to A3-3 did not exhibit a formation of the light scattering layer inside the enamel of the teeth.

The mouth refreshers of Examples A4-1 to A4-3 exhibited a formation of the light scattering layer inside the enamel of the teeth and whitening effect. By contrast, because the mouth refresher of Comparative Example A4-1 contained the organic acid but the fluoride ion supplying compound, and that of Comparative Example A4-2 contained the fluoride ion supplying compound but the organic acid nor inorganic acid, and that of Comparative Example A4-3 contained an excessively large amount of the organic acid, these Comparative Examples A4-1 to A4-3 did not exhibit a formation of the light scattering layer inside the enamel of the teeth.

The chewing gums of Examples A5-1 to A5-3 exhibited a formation of the light scattering layer inside the enamel of the teeth and whitening effect. In contrast, because the chewing gum of Comparative Example A5-1 contained the organic acid but the fluoride ion supplying compound, and that of Comparative Example A5-2 contained the fluoride ion supplying compound but the organic acid nor inorganic acid, and that of Comparative Example A5-3 contained an excessively large amount of the organic acid, these Comparative Example A5-1 to A5-3 did not exhibit a formation of the light scattering layer inside the enamel of the teeth.

Example B SERIES

<Preparation of Oral Preparation>

Toothpastes of Examples B1 to B3 and Comparative Examples B1 to B3 were prepared according to compositions as shown in Table B1. Liquid dentifrices of Examples B4 to B6 and Comparative Examples B4 to B6 were prepared according to compositions as shown in Table B2. Mouthwashes of Examples B7 to B9 and Comparative Examples B7 to B9 were prepared according to compositions as shown in Table B3.

TABLE B1

Toothpaste

| Component (wt %) | EXAMPLE B1 | EXAMPLE B2 | EXAMPLE B3 | COMPARATIVE EXAMPLE B1 | COMPARATIVE EXAMPLE B2 | COMPARATIVE EXAMPLE B3 |
|---|---|---|---|---|---|---|
| Malic acid | 2 | | 1 | 2 | 10 | 10 |
| Tartaric acid | | 2 | | | | |
| Citric acid | | | 0.5 | | | |
| Sodium hydroxide solution (48%) | | | | 1 | 5 | |
| Potassium hydroxide solution (48%) | 2 | 2 | 2 | | | |
| arginine | | | | | | 8 |
| Sodium fluoride | 0.21 | 0.1 | 0.21 | 0.21 | 0.21 | 0.21 |
| Sodium monofluorophosphate | | 0.35 | | | | |
| Sorbit solution | 30 | 30 | 30 | 30 | 30 | 30 |
| Propylene glycol | 5 | 5 | 5 | 5 | 5 | 5 |
| Sodium saccharin | 0.1 | 0.1 | 0.1 | 0.1 | 0.1 | 0.1 |
| Sodium carboxy methylcellulose | 1.5 | 1.5 | 1.5 | 1.5 | 1.5 | 1.5 |
| Thickening silica | 5 | 5 | 5 | 5 | 5 | 5 |
| Abrasive silica | 15 | 15 | 15 | 15 | 15 | 15 |
| Sodium laurylsulfate | 1.5 | 1.5 | 1.5 | 1.5 | 1.5 | 1.5 |
| Flavor | 1 | 1 | 1 | 1 | 1 | 1 |
| Purified water | q.s.*[1] | q.s.*[1] | q.s.*[1] | q.s.*[1] | q.s.*[1] | q.s.*[1] |
| (Total) | 100.0 | 100.0 | 100.0 | 100.0 | 100.0 | 100.0 |
| Taste | passed | passed | passed | passed | failed | failed |
| light scattering layer | ○ | ○ | ○ | X | X | X |
| whitening effect | ⊚ | ⊚ | ⊚ | X | ○ | ○ |

*[1]quantum sufficit

TABLE B2 liquid dentifrice

| Component (wt %) | EXAMPLE B4 | EXAMPLE B5 | EXAMPLE B6 | COMPARATIVE EXAMPLE B4 | COMPARATIVE EXAMPLE B5 | COMPARATIVE EXAMPLE B6 |
|---|---|---|---|---|---|---|
| Malic acid | 2 | | 1 | 2 | 10 | 10 |
| Tartaric acid | | 2 | | | | |
| Citric acid | | | 0.5 | | | |
| Sodium hydroxide solution (48%) | | | | 1 | 5 | |
| Potassium hydroxide solution (48%) | 2 | 2 | 2 | | | |
| Arginine | | | | | | 8 |
| Sodium fluoride | 0.21 | 0.1 | 0.21 | 0.21 | 0.21 | 0.21 |
| Sodium monofluorophosphate | | 0.35 | | | | |
| Sorbit solution | 30 | 30 | 30 | 30 | 30 | 30 |
| Propylene glycol | 5 | 5 | 5 | 5 | 5 | 5 |
| Sodium saccharin | 0.1 | 0.1 | 0.1 | 0.1 | 0.1 | 0.1 |
| Sodium carboxy methylcellulose | 0.8 | 0.8 | 0.8 | 0.8 | 0.8 | 0.8 |
| Thickening silica | 2 | 2 | 2 | 2 | 2 | 2 |
| Abrasive silica | 15 | 15 | 15 | 15 | 15 | 15 |
| Sodium laurylsulfate | 1.5 | 1.5 | 1.5 | 1.5 | 1.5 | 1.5 |
| Flavor | 1 | 1 | 1 | 1 | 1 | 1 |
| Purified water | q.s.*[1] | q.s.*[1] | q.s.*[1] | q.s.*[1] | q.s.*[1] | q.s.*[1] |
| (Total) | 100.0 | 100.0 | 100.0 | 100.0 | 100.0 | 100.0 |
| Taste | passed | passed | passed | passed | failed | failed |
| light scattering layer | ○ | ○ | ○ | X | X | X |
| whitening effect | ⊚ | ⊚ | ⊚ | X | ○ | ○ |

*[1]quantum sufficit

TABLE B3

| | Mouthwash | | | | | |
|---|---|---|---|---|---|---|
| | EXAMPLE | | | COMPARATIVE EXAMPLE | | |
| Component (wt %) | B7 | B8 | B9 | B7 | B8 | B9 |
| Malic acid | 2 | | 1 | 2 | 10 | 10 |
| Tartaric acid | | 2 | | | | |
| Citric acid | | | 0.5 | | | |
| Sodium hydroxide solution (48%) | | | | 1 | 5 | |
| Potassium hydroxide solution (48%) | 2 | 2 | 2 | | | |
| Arginine | | | | | | 8 |
| Sodium fluoride | 0.21 | 0.1 | 0.21 | 0.21 | 0.21 | 0.21 |
| Sodium monofluorophosphate | | 0.35 | | | | |
| Sorbit solution | 30 | 30 | 30 | 30 | 30 | 30 |
| Sodium saccharin | 0.01 | 0.01 | 0.01 | 0.01 | 0.01 | 0.01 |
| Polyoxyethylene hydrogenated caster oil | 0.5 | 0.5 | 0.5 | 0.5 | 0.5 | 0.5 |
| Flavor | 0.2 | 0.2 | 0.2 | 0.2 | 0.2 | 0.2 |
| Purified water | q.s.*[1] | q.s.*[1] | q.s.*[1] | q.s.*[1] | q.s.*[1] | q.s.*[1] |
| (Total) | 100.0 | 100.0 | 100.0 | 100.0 | 100.0 | 100.0 |
| Taste | passed | passed | passed | passed | failed | failed |
| light scattering layer | ○ | ○ | ○ | X | X | X |
| whitening effect | ⊚ | ⊚ | ⊚ | X | ○ | ○ |

*[1] quantum sufficit

<Evaluating Method>

(1) Evaluation of Taste

Ten persons (five males, five females) of the test subject brushed for about 2 min as they like by their routinely-using toothbrush with 1 g of the toothpastes or liquid dentifrices, then the taste of each toothpaste and liquid dentifrice were evaluated according to the following criteria. As to the mouthwashes, the test subjects put 5 ml of the each mouthwash in their mouth, and then washed out for about 15 sec with the mouthwash, and thereafter the mouthwashes was also evaluated as well according to the following criteria.

That is, an acceptable case was shown as "○", an unacceptable case was shown as "×". Then the case that more than half of the results were acceptable was shown as "passed", the other cases were shown as "failed".

(2) Presence or No-Presence of Light Scattering Layer

The each composition as shown in Table B1 and Table B2 was diluted with ion-exchanged water to 30 wt. %, then a bovine tooth (having a mirror polished surface) was immersed in the diluted solution for 40 hours. Also, another bovine tooth (having a mirror polished surface) was immersed in the each composition shown in Table B3 for 40 hours.

After the treatments, whether a light scattering layer is formed or not is evaluated by the same procedure of the evaluating method (1) employed in Example A series. The results are shown in Table B4. By the treatment of the oral preparation of the present invention, b* value was decreased widely, and closed almost 0. From this result, the fact that the tooth piece lost yellowness and attained whiteness was confirmed.

TABLE B4

| | L* | a* | b* |
|---|---|---|---|
| Treatment with the present invention | 78.2 | 5.81 | 4.11 |
| No treatment | 76.4 | 5.73 | 10.3 |
| Color difference | +1.8 | +0.08 | −6.19 |

The longitudinal section of the bovine tooth which was confirmed to become white by the treatment of the oral preparation of the each Example was evaluated by the same procedure and criteria of the evaluating methods employed in Example A series. A sample which had a light scattering layer was shown as "○", and a sample which did not have any light scattering layer was shown as "×".

(3) Presence or No-Presence of Whitening Effect

The each composition as shown in Table B1 and Table B2 was diluted with ion-exchanged water to 30 wt. %, then a bovine tooth (having a mirror polished surface), which had been photographed in advance, was immersed in the diluted solution for 40 hours. Also, another bovine tooth (having a mirror polished surface), which had been photographed in advance, was immersed in the each composition shown in Table B3 for 40 hours.

After the treatment, the tooth was taken out from the solution and photographed again, and the result was evaluated by the following criteria. A panel of 15 experts was asked to see the photographs of the tooth before and after the treatment, and to evaluate whether the tooth turned white or not. In the case that the panel confirmed that the tooth turned white but lost gloss, the tooth was classified as an unchanged tooth, even though it had turned white. The tooth which all of them judged to turn white was evaluated as "⊚", the tooth which half or more of them judged to turn white was evaluated as "○", and remaining teeth were evaluated as "×". The each result was shown in Tables B1-B3.

<Overall Results>

In the toothpastes of Examples B1 to B3, . the addition of potassium ion allowed a reduced amount of the organic and/or inorganic acid to fulfill an effective amount thereof, and therefore these toothpastes exhibited a formation of the light scattering layer inside the enamel of the teeth, and excellent whitening effect. Further, each taste of them was also good because amount of the acid was small.

In contrast, because the toothpaste of Comparative Example B1 contained only small amount of the organic acid and/or inorganic acid, the toothpaste provided a good taste but did not exhibit a formation of the light scattering layer nor whitening effect. Also, because the toothpastes of Comparative Examples B2 and B3 contained too much amount of the organic acid and/or inorganic acid, the toothpastes exhibited no formation of a light scattering layer and also provided rather lower whitening effect, and a poor taste.

In the liquid dentifrices of Examples B4 to B6, . the addition of potassium ion allowed a reduced amount of the organic and/or inorganic acid to fulfill an effective amount thereof, and therefore these liquid dentifrices exhibited a formation of the light scattering layer inside the enamel of the teeth, and excellent whitening effect. Further, each taste of them was also good because amount of the acid was small.

In contrast, because the liquid dentifrice of Comparative Example B4 contained only small amount of the organic acid and/or inorganic acid, the liquid dentifrice provided a good taste but did not exhibit a formation of the light scattering layer nor whitening effect. Also, because the liquid dentifrices of Comparative Examples B5 and B6 contained too much amount of the organic acid and/or inorganic acid, the liquid dentifrices provided a poor taste, no formation of a light scattering layer and rather lower whitening effect.

In the mouthwashes of Examples B7 to B9, . the addition of potassium ion allowed a reduced amount of the organic and/or inorganic acid to fulfill an effective amount thereof, and therefore these mouthwashes exhibited a formation of the light scattering layer inside the enamel of the teeth, and excellent whitening effect. Further, taste was also good because amount of the acid was small.

In contrast, because the mouthwash of Comparative Example B7 contained only small amount of the organic acid and/or inorganic acid, the mouthwash provided a good taste but no whitening effect. Also, because the mouthwashes of Comparative Examples B8 and B9 contained too much amount of the organic acid and/or inorganic acid, the mouthwashes provided bad taste, no formation of a light scattering layer and rather lower whitening effect.

Example C Series

<Preparation of Oral Preparation>

Toothpastes of Examples C1 to C3 and Comparative Examples C1 were prepared according to the compositions as shown in Table C1. Liquid dentifrices of Examples C4 to C6 and Comparative Examples C2 were prepared according to the compositions as shown in Table C2. Mouthwashes of Examples C7 to C9 and Comparative Examples C3 were prepared according to the compositions as shown in Table C3.

TABLE C1

| | Toothpaste | | | |
|---|---|---|---|---|
| | EXAMPLE | | | COMPARATIVE EXAMPLE |
| Component (wt %) | C1 | C2 | C3 | C1 |
| DL-Malic acid | 2*1 | | 1*4 | |
| Tartaric acid | | 2*3 | 1*5 | |
| Lactic acid | | | | 7*6 |
| Sodium hydroxide solution (48%) | | | | 4.7*7 |
| Potassium hydroxide solution (48%) | 2*2 | 2 | 2 | |
| Sodium fluoride | 0.21*8 | 0.21*8 | 0.21*8 | 0.21*8 |
| Calcium chloride | | | | 1 |
| Sorbit solution | 30 | 30 | 30 | 30 |
| PEG600 | 5 | 5 | 5 | 5 |
| Sodium saccharin | 0.1 | 0.1 | 0.1 | 0.15 |
| Sodium carboxy methylcellulose | 1.5 | 1.5 | 1.5 | 1.5 |
| Thickening silica | 5 | 5 | 5 | 5 |
| Abrasive silica | 15 | 15 | 15 | 15 |
| Sodium laurylsulfate | 1.5 | 1.5 | 1.5 | 1.5 |
| Flavor | 1 | 1 | 1 | 1 |
| Purified water | q.s.*9 | q.s.*9 | q.s.*9 | q.s.*9 |
| (Total) | 100.0 | 100.0 | 100.0 | 100.0 |
| pH | 4.5 | 4.5 | 4.5 | 4.5 |
| Taste | passed | passed | passed | failed |
| whitening effect | ○ | ○ | ○ | X |

*1 corresponding to 0.15 mol/kg
*2 corresponding to 0.13 mol/kg (in terms of potassium ion)
*3 corresponding to 0.13 mol/kg
*4 corresponding to 0.08 mol/kg
*5 corresponding to 0.07 mol/kg
*6 corresponding to 0.78 mol/kg
*7 corresponding to 0.47 mol/kg (in terms of sodium ion)
*8 corresponding to 0.1 wt. % (in terms of fluoride ion)
*9 quantum sufficit

TABLE C2

| | Liquid dentifrice | | | |
|---|---|---|---|---|
| | EXAMPLE | | | COMPARATIVE EXAMPLE |
| Component (wt %) | C4 | C5 | C6 | C2 |
| DL-Malic acid | 2*1 | | 1*4 | |
| Tartaric acid | | 2*3 | 1*5 | |
| Lactic acid | | | | 7*6 |
| Sodium hydroxide solution (48%) | | | | 4.7*7 |
| Potassium hydroxide solution (48%) | 2*2 | 2 | 2 | |
| Sodium fluoride | 0.21*8 | 0.21*8 | 0.21*8 | 0.21*8 |
| Calcium chloride | | | | 1 |
| Sorbit solution | 30 | 30 | 30 | 30 |
| PEG600 | 5 | 5 | 5 | 5 |
| Sodium saccharin | 0.1 | 0.1 | 0.1 | 0.15 |
| Sodium carboxy methylcellulose | 0.8 | 0.8 | 0.8 | 0.8 |
| Thickening silica | 2 | 2 | 2 | 2 |
| Abrasive silica | 15 | 15 | 15 | 15 |
| Sodium laurylsulfate | 1.5 | 1.5 | 1.5 | 1.5 |
| Flavor | 1 | 1 | 1 | 1 |
| Purified water | q.s.*9 | q.s.*9 | q.s.*9 | q.s.*9 |
| (Total) | 100.0 | 100.0 | 100.0 | 100.0 |
| pH | 4.5 | 4.5 | 4.5 | 4.5 |
| taste | passed | passed | passed | failed |
| whitening effect | ○ | ○ | ○ | X |

*1 corresponding to 0.15 mol/kg
*2 corresponding to 0.13 mol/kg (in terms of potassium ion)
*3 corresponding to 0.13 mol/kg
*4 corresponding to 0.08 mol/kg
*5 corresponding to 0.07 mol/kg
*6 corresponding to 0.78 mol/kg
*7 corresponding to 0.47 mol/kg (in terms of sodium ion)
*8 corresponding to 0.1 wt. % (in terms of fluoride ion)
*9 quantum sufficit

TABLE C3

Mousewash

| Component (wt %) | EXAMPLE C7 | EXAMPLE C8 | EXAMPLE C9 | COMPARATIVE EXAMPLE C3 |
|---|---|---|---|---|
| DL-Malic acid | 2*[1] | | 1*[4] | |
| Tartaric acid | | 2*[3] | 1*[5] | |
| Lactic acid | | | | 7*[6] |
| Sodium hydroxide solution (48%) | | | | 4.7*[7] |
| Potassium hydroxide solution (48%) | 2*[2] | 2 | 2 | |
| Sodium fluoride | 0.21*[8] | 0.21*[8] | 0.21*[8] | 0.21*[8] |
| Calcium chloride | | | | 1 |
| Sorbit solution | 30 | 30 | 30 | 30 |
| ethanol | 5 | 5 | 5 | 5 |
| Sodium saccharin | 0.01 | 0.01 | 0.01 | 0.01 |
| Polyoxyethylene hydrogenated castor oil | 0.5 | 0.5 | 0.5 | 0.5 |
| Flavor | 0.2 | 0.2 | 0.2 | 0.2 |
| Purified water | q.s.*[9] | q.s.*[9] | q.s.*[9] | q.s.*[9] |
| (Total) | 100.0 | 100.0 | 100.0 | 100.0 |
| pH | 4.5 | 4.5 | 4.5 | 4.5 |
| taste | passed | passed | passed | failed |
| whitening effect | ○ | ○ | ○ | X |

*[1]corresponding to 0.15 mol/kg
*[2]corresponding to 0.13 mol/kg (in terms of potassium ion)
*[3]corresponding to 0.13 mol/kg
*[4]corresponding to 0.08 mol/kg
*[5]corresponding to 0.07 mol/kg
*[6]corresponding to 0.78 mol/kg
*[7]corresponding to 0.47 mol/kg (in terms of sodium ion)
*[8]corresponding to 0.1 wt. % (in terms of fluoride ion)
*[9]quantum sufficit <Evaluating Method>

(1) Evaluation of Taste

Fifteen persons as the test subject attended, and the taste of the oral preparation of the each Example was evaluated by the same procedure and criteria of the evaluating method (1) employed in Example B series.

(2) Presence or No-Presence of Whitening Effect

Each composition of Example C series was diluted with ion-exchanged water to 30 wt. %, then a bovine tooth (having a mirror polished surface), which had been photographed in advance, was immersed in the diluted solution for 40 hours. After the treatment the tooth was taken out from the solution and photographed again to compare its color with the tooth before the treatment, and the whitening effect was evaluated by the same procedure and criteria of the evaluating method (3) employed in Example B series.

<Overall Results>

In the toothpastes of Examples C1 to C3, . the addition of potassium ion allowed a reduced amount of the organic and/or inorganic acid to fulfill an effective amount thereof, and these toothpastes exhibited an excellent whitening effect. Further, taste was also good because the amount of the acid was small.

In contrast, since the toothpastes of Comparative Example C1 contained a large amount of the organic acid, it provided a poor taste. Further, since the toothpastes of Comparative Examples C1 contained a calcium ion, it also provided a poor whitening effect.

In the liquid dentifrices of Examples C4 to C6, . the addition of a potassium ion allowed a reduced amount of the organic and/or inorganic acid to fulfill an effective amount thereof, and these liquid dentifrices exhibited an excellent whitening effect. Further, taste was also good because the amount of the acid was small.

In contrast, since the liquid dentifrices of Comparative Example C2 contained a large amount of the organic acid, it provided a poor taste. Further, since the liquid dentifrices of Comparative Example C2 contained a calcium ion, it also provided a poor whitening effect.

In the mouthwashes of Examples C7 to C9, . the addition of a potassium ion allowed a reduced amount of the organic and/or inorganic acid to fulfill an effective amount thereof, and these mouthwashes exhibited an excellent whitening effect. Further, taste was also good because the amount of the acid was small.

In contrast, since the mouthwashes of Comparative Example 3 contained a large amount of the organic acid, it provided a poor taste. Further, since the mouthwashes of Comparative Example C3 contained a calcium ion, it also provided a poor whitening effect.

The invention claimed is:

1. A method for forming a light scattering layer inside enamel of teeth, the method comprising:
   applying an oral preparation to teeth in which an endogenous colored substance is deposited in the depth of the enamel,
   wherein said oral preparation comprises:
   (A) from 0.02 to 0.2 wt. %, in terms of fluorine atom, of a fluoride ion supplying component which is at least one selected from the group consisting of sodium fluoride, sodium monofluorophosphate, lithium fluoride, ammonium fluoride, and a mixture thereof;
   (B) from 0.03 to 0.3 mol/kg of a combination of at least one organic acid selected from the group consisting of malic acid, tartaric acid, and a mixture thereof with a salt of the organic acid;
   (C) from 0.03 to 0.5 mol/kg of potassium ion; and
   (D) water; and
   wherein said oral preparation has a pH ranging from 3 to 5.5 when diluted with water to 30 wt. %.

2. The method for forming a light scattering layer according to claim 1, wherein the light scattering layer is formed at a depth of 500 μm or less from the surface of the enamel.

3. The method for forming a light scattering layer according to claim 1, wherein no calcium ion is contained.

4. An oral preparation comprising:
   (A) from 0.02 to 0.2 wt. %, in terms of fluorine atom, of a fluoride ion supplying component which is at least one selected from the group consisting of sodium fluoride, sodium monofluorophosphate, lithium fluoride, ammonium fluoride, and a mixture thereof;
   (B) from 0.03 to 0.3 mol/kg of a combination of at least one organic acid selected from the group consisting malic acid, tartaric acid, and a mixture thereof, with a salt of the organic acid;
   (C) from 0.03 to 0.5 mol/kg of potassium ion; and
   (D) water; and
   wherein said oral preparation has a pH ranging from 3 to 5.5 when diluted with water to 30 wt. %.

5. The oral preparation according to claim 4, wherein a light scattering layer is formed inside enamel of the teeth when the oral preparation is applied to the teeth in which an endogenous colored substance is deposited in the depth of the enamel.

6. The oral preparation according to claim 5, wherein the light scattering layer is formed at a depth of 500 μm or less from the surface of the enamel.

7. The oral preparation according to claim 4, wherein no calcium ion is contained.

* * * * *